United States Patent [19]

Saville

[11] Patent Number: Plant 5,749

[45] Date of Patent: Jun. 17, 1986

[54] ROSE PLANT

[75] Inventor: F. Harmon Saville, Rowley, Mass.

[73] Assignee: Nor'East Miniature Roses, Inc., Rowley, Mass.

[21] Appl. No.: 653,352

[22] Filed: Sep. 24, 1984

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety with currant red blooms of good exhibition form retaining its warm, red coloring.

1 Drawing Figure

The present invention relates to a new and distinct variety of rose plant of the miniature rose class, which was originated by my crossing as seed parent the rose known as "Baby Katie" and an unpatented, unnamed seedling of my creation as pollen parent. The varietal denomination of this new variety is "Savacamp".

Among the novel characteristics possessed by this new variety which distinguish it from its parents and all other varieties of which I am aware are its unusually stable currant red flowers of exhibition form which are attractively set off by leathery green foliage and which are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Seedling.

*Seed parent.*—"Baby Katie".

*Pollen parent.*—Unnamed seedling.

Class: Miniature.

The following observations are made of specimens grown outdoors in Essex County, Mass., during the month of July.

1. FLOWER

Blooming habit: Profuse, recurrent.

A. Bud:

(1) *Size.*—Medium.

(2) *Form.*—Ovate, pointed.

(3) *Color.*—When sepals first divide and petals begin to unfurl — currant red 46A.

(4) *Sepals.*—Longer than bud, relatively smooth.

(5) *Peduncle.*—Length — About $1\frac{3}{4}$ inches. Aspect — Straight. Strength — Erect. Color — Near 14A but darkens quickly to brownish green.

B. Bloom:

(1) *Size.*—Average size when fully expanded — about 1 inch.

(2) *Borne.*—Singly and sprays.

(3) *Form.*—High centered through $\frac{3}{4}$ open stage, becoming flat, petals roll under upon opening; flower maintains symmetrical exhibition form.

(4) *Petalage.*—Number of petals under normal conditions — about 20 to 25.

(5) *Color.*—Color remains consistent from opening bud stage through exhibition ($\frac{1}{3}$ to $\frac{3}{4}$ open) stage, maintaining bright currant red 45A appearance. Petal undersurface and general tonality from a distance also appears substantially color constant 45A.

C. Petals:

(1) *Texture.*—Thick.

(2) *Appearance.*—Inside — satiny, outside — satiny.

(3) *Form.*—Wide oval, fan shaped.

(4) *Arrangement.*—Regularly arranged, shingle-like.

(5) *Petaloids in center.*—Few.

(6) *Persistence.*—Persistent but then drop off cleanly.

(7) *Fragrance.*—None.

(8) *Lasting quality.*—Long lasting on plant and long lasting as cut flower.

2. REPRODUCTIVE ORGANS

A. Stamens, filaments and anthers:

(1) *Arrangement.*—Regularly arranged around styles.

(2) *Color.*—Near 17A.

B. Pollen:

*Color.*—Near 17A.

C. Styles: Even, medium length.

D. Stigmas:

*Color.*—Near 2D.

E. Hips: None observed.

3. PLANT

A. Form: Bushy, compact, symmetrical.

B. Growth: Vigorous, well branched.

*Height attained.*—About 10 to 14 inches.

C. Foliage: Compound 5 to 7 leaflets.

(1) *Size.*—Medium.

(2) *Quantity.*—Abundant.

(3) *Color.*—New foliage: Upper side — Near to 147A. Under side — Near to 148B. Old foliage: Upper side — Near 147A. Under side — Near 148B.

(4) *Shape.*—Oval, pointed.

(5) *Texture.*—Upper side is leathery and under side is matte.

(6) *Edge.*—Serrated.

(7) *Serration.*—Even.

(8) *Leaf stem.*—Color — Near to 148A. Under side — Near 146C.

(9) *Stipules.*—Medium, relatively smooth.

(10) *Resistance to disease.*—Blackspot — average. Mildew — Average. Rust — Average.

D. Wood:

(1) *New wood.*—Color — Near 146C. Bark — Smooth.

(2) *Old wood.*—Color — Near 146A. Bark — Smooth.

E. Thorns:

(1) *Thorns.*—Quantity (main stalk): ordinary. On laterals from stalk — Few. Form — Short, pointed, angled slightly downward. Length — Medium. Color — Near 183A. Position — Irregular.

(2) *Prickles.*—Few.

F. Winter hardiness: Requires ordinary protection in extreme climates.

I claim:

1. A new and distinct variety of rose plant of the miniature rose class, substantially as shown and described, characterized particularly by unusually stable currant red flowers of good exhibition form attractively set off by leathery green foliage.

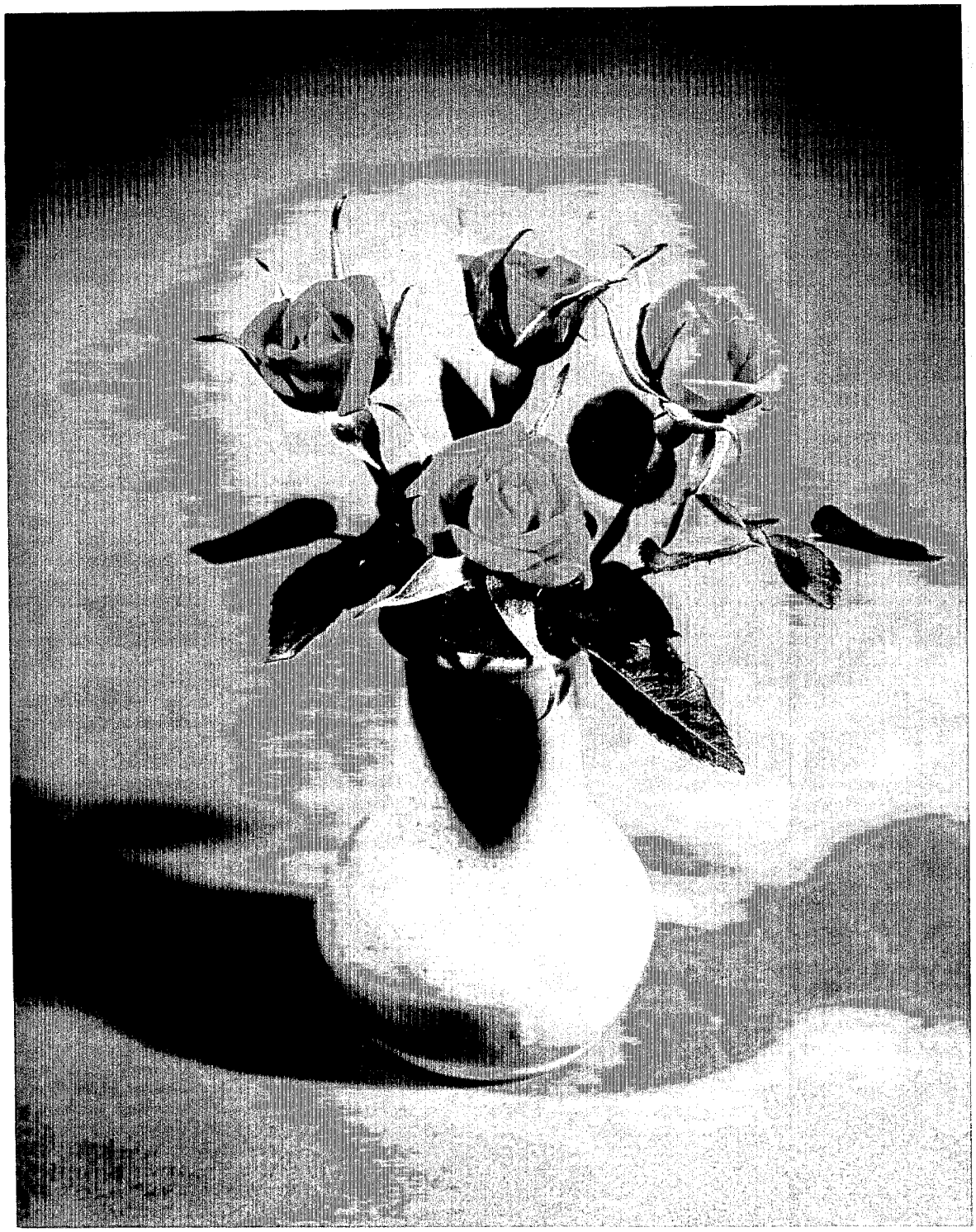

* * * * *